(12) United States Patent
Wu et al.

(10) Patent No.: US 10,662,078 B1
(45) Date of Patent: May 26, 2020

(54) UV STERILIZATION TUBE

(71) Applicant: Purity (Xiamen) Sanitary Ware Co., Ltd., Xiamen, Fujian (CN)

(72) Inventors: James Wu, Taichung (TW); Alex Wu, Taichung (TW); Ce-Wen Yang, Xiamen (CN)

(73) Assignee: PURITY (XIAMEN) SANITARY WARE CO., LTD., Xiamen (CN)

( * ) Notice: Subject to any disclaimer, the term of this patent is extended or adjusted under 35 U.S.C. 154(b) by 0 days.

(21) Appl. No.: 16/391,695

(22) Filed: Apr. 23, 2019

(51) Int. Cl.
*A61L 2/10* (2006.01)
*C02F 1/32* (2006.01)

(52) U.S. Cl.
CPC .............. *C02F 1/32* (2013.01); *A61L 2/10* (2013.01); *C02F 2201/328* (2013.01); *C02F 2201/3222* (2013.01); *C02F 2201/3228* (2013.01); *C02F 2303/04* (2013.01)

(58) Field of Classification Search
CPC ............. C02F 1/32; C02F 2201/3222; C02F 2201/3228; C02F 2201/328; C02F 2303/04; A61L 2/10
USPC ....... 250/436, 453.11, 454.11, 455.11, 504 R
See application file for complete search history.

(56) References Cited

U.S. PATENT DOCUMENTS

| 7,270,748 B1 * | 9/2007 | Lieggi | C02F 1/325 210/198.1 |
| 2005/0077732 A1 * | 4/2005 | Baarman | C02F 1/325 290/54 |
| 2017/0088440 A1 * | 3/2017 | Lin | C02F 1/325 |

* cited by examiner

*Primary Examiner* — Nicole M Ippolito
(74) *Attorney, Agent, or Firm* — Birch, Stewart, Kolasch & Birch, LLP

(57) ABSTRACT

A UV sterilization tube includes a hollow tube, a hydroelectric power module and a UV sterilization module. The hollow tube includes an inlet end and an outlet end communicating with each other. The hydroelectric power module is positioned in the hollow tube, and communicates with the inlet end and the outlet end of the hollow tube, wherein the hydroelectric power module generates electric power by a water flow. The UV sterilization module is positioned in the hollow tube, and is electrically connected to the hydroelectric power module. The UV sterilization module includes a UV source and a reflector, wherein the UV source has a light-emitting surface facing to the reflector. A sterilization channel, which communicates with the inlet end and the outlet end of the hollow tube, is between the UV source and the reflector.

18 Claims, 3 Drawing Sheets

UV STERILIZATION TUBE

BACKGROUND OF THE INVENTION

1. Technical Field

The present disclosure relates generally to a UV sterilization device, and more particularly to a UV sterilization tube to provide sterilized water.

2. Description of Related Art

With the advancement of society and industry, people's requirements for quality of life are getting higher and higher.

As far as the quality of water used in daily life is concerned, whether it is bathing water, washing water for fruits and vegetables, or drinking water, users often connect tap water to water filtering equipment to remove bacteria, impurities and pollutants. However, there may still be many bacteria or viruses in the filtered water flowing out of the water filtering equipment, and generally, the filtered water cannot be directly consumed. The filtered water needs to be further boiled in order to be completely sterilized.

In recent years, a UV sterilization equipment that can be connected in series with a water filtration equipment has appeared on the market. With the UV sterilizing equipment, the filtered water flowing out of the water filtering equipment can be further thoroughly sterilized and disinfected. However, the conventional UV sterilization equipment needs external power supply and is bulky, so that it needs to install the conventional UV sterilization equipment close to the socket, and needs to make an enough space to install the conventional UV sterilization equipment.

At least for the above reasons, the conventional UV sterilization device still have room for improvements.

BRIEF SUMMARY OF THE INVENTION

In view of the above, the primary objective of the present disclosure is to provide a UV sterilization tube which has a slim size and does not need external power supply, so that the UV sterilization tube is convenient to use.

The present disclosure provides a UV sterilization tube. The UV sterilization tube includes a hollow tube, a hydroelectric power module and a UV sterilization module. The hollow tube includes an inlet end and an outlet end communicating with each other. The hydroelectric power module is positioned in the hollow tube, and communicates with the inlet end and the outlet end of the hollow tube, wherein the hydroelectric power module generates electric power by a water flow. The UV sterilization module is positioned in the hollow tube, and is electrically connected to the hydroelectric power module. The UV sterilization module includes a UV source and a reflector, wherein the UV source has a light-emitting surface facing to the reflector. A sterilization channel is between the UV source and the reflector, and the sterilization channel communicates with the inlet end and the outlet end of the hollow tube.

With the aforementioned design, the UV sterilization tube includes a hydroelectric power module which could generates electric power by a water flow, whereby to provide the electric power to the UV sterilization module. Thereby, the UV sterilization tube provided in the present invention does not need external power supply, which is no need to be installed close to a socket. Furthermore, the UV sterilization tube provided in the present invention has a slim size, so that there is no need to make an enough space to install the UV sterilization tube.

BRIEF DESCRIPTION OF THE SEVERAL VIEWS OF THE DRAWINGS

The present disclosure will be best understood by referring to the following detailed description of some illustrative embodiments in conjunction with the accompanying drawings, in which.

DETAILED DESCRIPTION OF THE INVENTION

Figure 1:
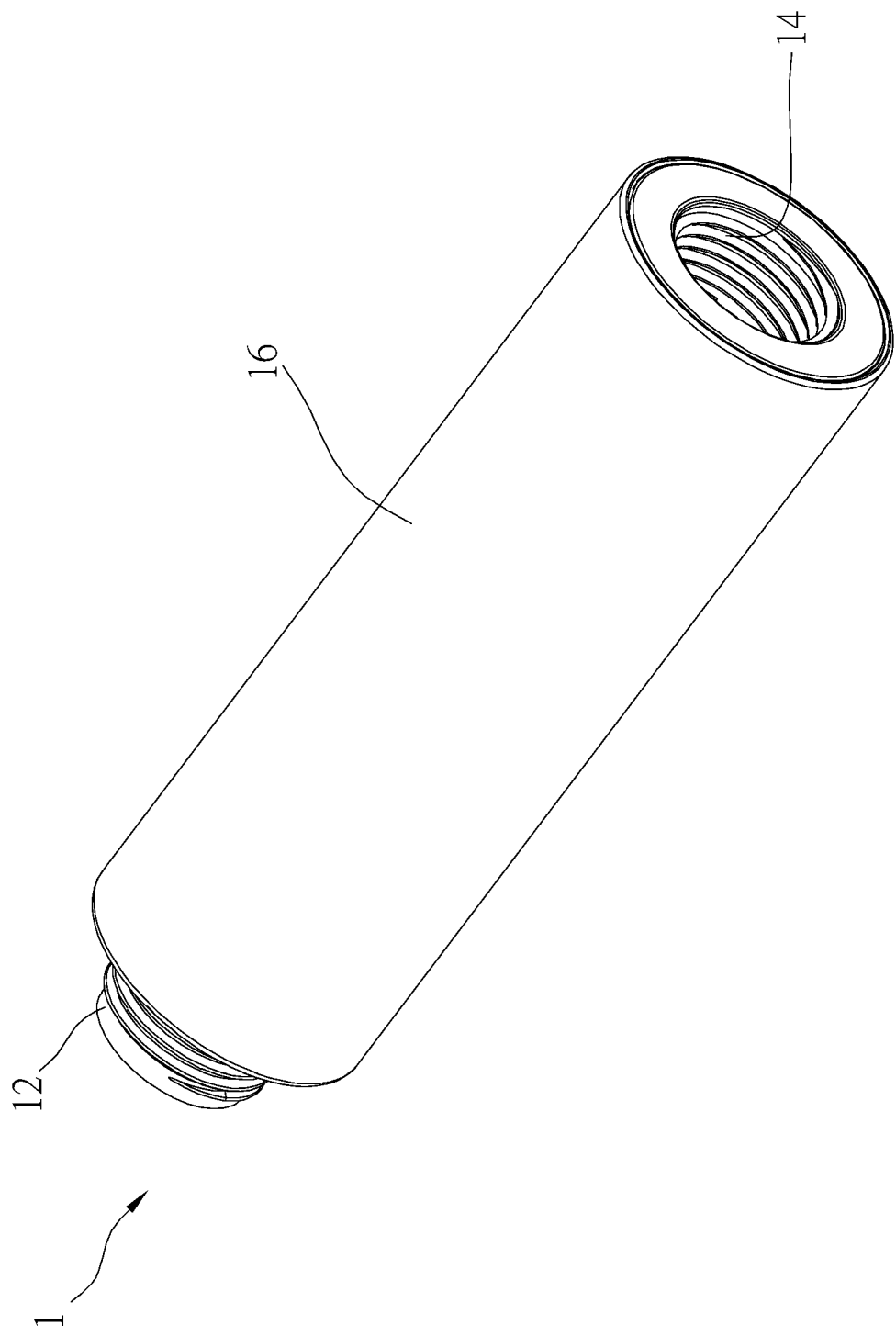
FIG. 1 is a perspective view of a UV sterilization tube of one embodiment of the present disclosure.
Figure 2:
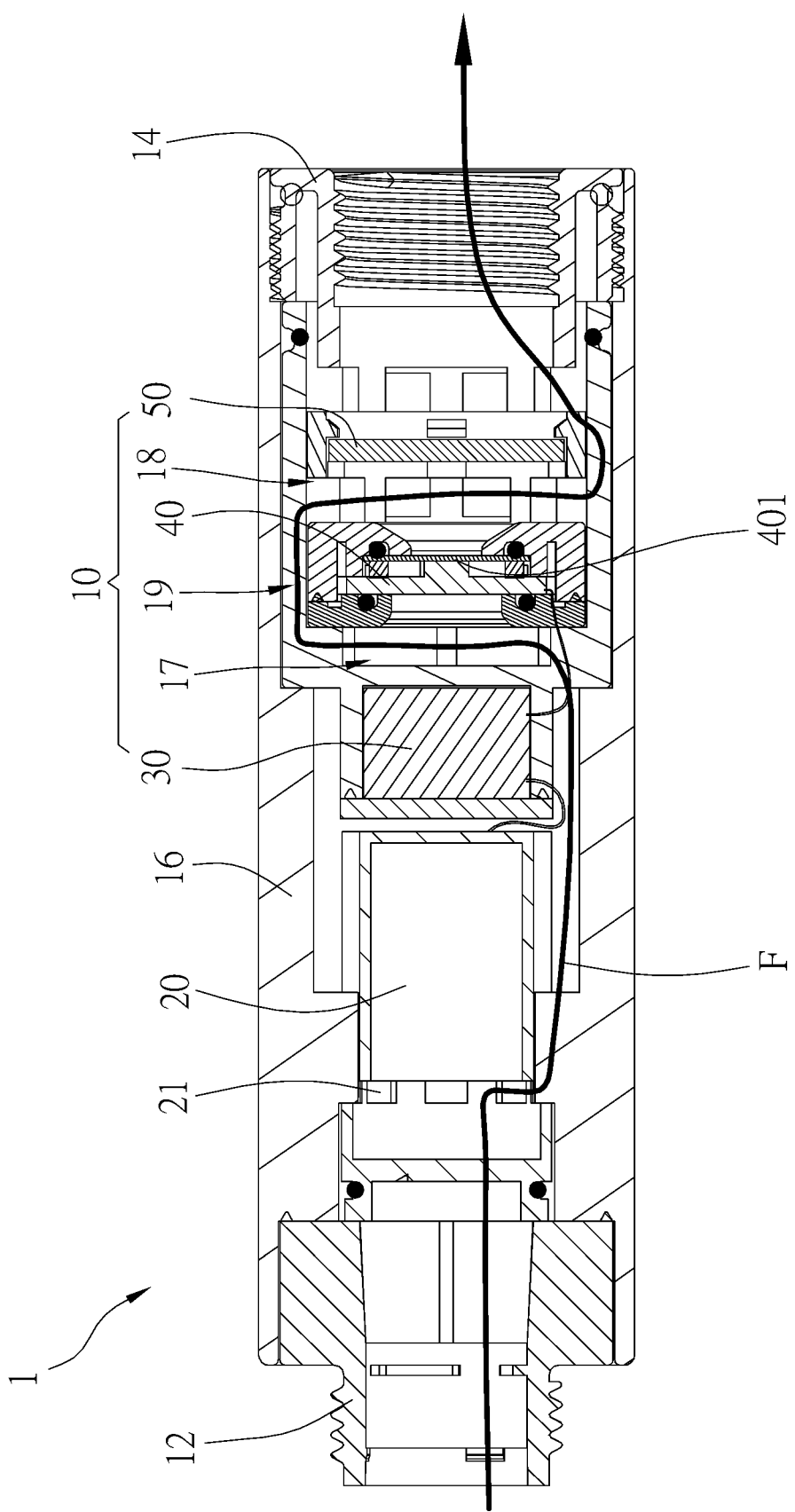
FIG. 2 is a cross-sectional view of the UV sterilization tube of one embodiment of the present disclosure.
Figure 3:
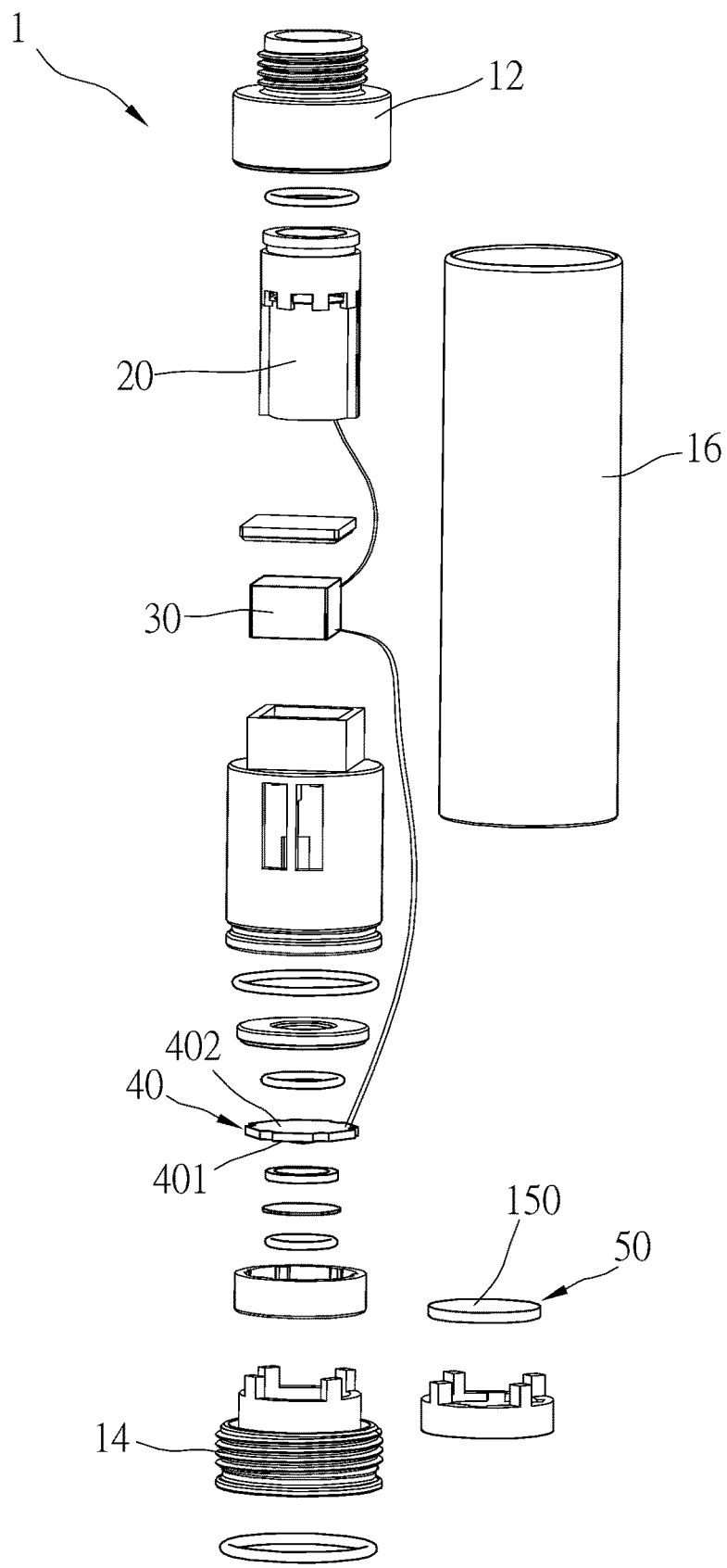
FIG. 3 is an exploded view of the UV sterilization tube of one embodiment of the present disclosure.

As illustrated in FIG. 1 to FIG. 3, a UV sterilization tube 1 is provided. The UV sterilization tube 1 includes a hollow tube 16, a hydroelectric power module 20 and a UV sterilization module 10. The hollow tube 16 includes an inlet end 12 and an outlet end 14 communicating with each other. The hydroelectric power module 20 is positioned in the hollow tube 16, and communicates with the inlet end 12 and the outlet end 14 of the hollow tube 16, wherein the hydroelectric power module 20 generates electric power by a water flow F.

The UV sterilization module 10 is positioned in the hollow tube 16, and is electrically connected to the hydroelectric power module 20. The UV sterilization module 10 includes a UV source 40 and a reflector 50, wherein the UV source 40 has a light-emitting surface 401 facing to the reflector 50. According to one embodiments of the present invention, a sterilization channel 18 is between the UV source 40 and the reflector 50, and the sterilization channel 18 communicates with the inlet end 12 and the outlet end 14 of the hollow tube 16. According to one embodiments of the present invention, the reflector 50 has a reflection surface 501 facing to the light-emitting surface 401 of the UV source 40.

The UV sterilization module 10 includes an electronic control member 30. The electronic control member 30 is electrically connected to the hydroelectric power module 20 and the UV source 40. According to one embodiments of the present invention, the UV source 40 has an electrical connection surface 402 which is electrically connected to the electronic control member 30. According to one embodiments of the present invention, a cooling channel 17 is between the electrical connection surface 402 of the UV source 40 and the electronic control member 30, the cooling channel 17 communicates with the inlet end 12 and the outlet end 14. According to one embodiments of the present invention, the cooling channel 17 is used to cool down the UV source 40 while the UV source 40 is emitting UV light, which would increase the temperature of the UV source 40.

As shown in FIG. 2, the water flow F flows through the cooling channel 17 and the sterilization channel 18. It is worthy to note that, the water flow F does not flow between the hydroelectric power module 20 and the electronic control member 30.

According to one embodiments of the present invention, one end of the cooling channel 17 is connected to the inlet end 12 of the hollow tube 16, and another end thereof is connected to the sterilization channel 18; further, one end of the sterilization channel 18 is connected to the outlet end 14 of the hollow tube 16, and another end thereof is connected to the cooling channel 17.

According to another one embodiments of the present invention, one end of the sterilization channel 18 could be connected to the inlet end 12 of the hollow tube 16, and another end thereof is connected to the cooling channel 17; further, one end of the cooling channel 17 could be connected to the outlet end 14 of the hollow tube 16, and another end thereof is connected to the sterilization channel 18.

As shown in FIG. 2, the cooling channel 17 and the sterilization channel 18 are connected to form a zigzag flow route. According to one embodiments of the present invention, the cooling channel 17 and the sterilization channel 18 are substantially parallel to each other, and the cooling channel 17 is connected to the sterilization channel 18 through a side channel 19. According to one embodiments of the present invention, since the cooling channel 17 and the sterilization channel 18 are connected to form a zigzag flow route, the flow rate of the water flow F would be slow down, whereby the water would slow flow through the sterilization channel 18, in order to make water to be thoroughly sterilized and disinfected.

Referring to FIG. 3, the electrical connected surface 402 and the light-emitting surface 401 of the UV light source 40 are positioned on different sides. According to one embodiments of the present invention, the electrical connected surface 402 and the light-emitting surface 401 of the UV light source 40 are positioned back-to-back. As shown in FIG. 2 and FIG. 3, the electrical connected surface 402 of the UV light source 40 faces to the electronic control member 30.

As shown in FIG. 2, the electronic control member 30 is positioned between the hydroelectric power module 20 and the UV source 40. According to one embodiments of the present invention, the UV source 40 is positioned between the electronic control member 30 and the reflector 50. According to one embodiments of the present invention, the hydroelectric power module 20 is positioned between the UV sterilization module 10 and the inlet end 12. According to one embodiments of the present invention, the hydroelectric power module 20 has a water-driven blade assembly 21 facing to the inlet end 12, whereby the water flow F may drive the water-driven blade assembly 21 to rotate.

In practice, the hydroelectric power module 20 could be positioned between the UV sterilization module 10 and the outlet end 14. According to another one embodiments of the present invention, the hydroelectric power module 20 has a water-driven blade assembly 21 positioned back-to-back to the outlet end 14, whereby the water flow F may drive the water-driven blade assembly 21 to rotate.

With the aforementioned design, the UV sterilization tube includes a hydroelectric power module which could generates electric power by a water flow, whereby to provide the electric power to the UV sterilization module. Thereby, the UV sterilization tube provided in the present invention does not need external power supply, which is no need to be installed close to a socket. Furthermore, the UV sterilization tube provided in the present invention has a slim size, so that there is no need to make an enough space to install the UV sterilization tube.

It must be pointed out that the embodiments described above are only some preferred embodiments of the present disclosure. All equivalent structures which employ the concepts disclosed in this specification and the appended claims should fall within the scope of the present disclosure.

What is claimed is:

1. A UV sterilization tube, comprising:
a hollow tube, comprising an inlet end and an outlet end communicating with each other;
a hydroelectric power module, positioned in the hollow tube, and communicating with the inlet end and the outlet end of the hollow tube, wherein the hydroelectric power module generates electric power by a water flow;
a UV sterilization module, positioned in the hollow tube, and electrically connected to the hydroelectric power module, the UV sterilization module comprises a UV source and a reflector, wherein the UV source has a light-emitting surface facing to the reflector, and a sterilization channel is between the UV source and the reflector, the sterilization channel communicates with the inlet end and the outlet end of the hollow tube.

2. The UV sterilization tube of claim 1, wherein the UV sterilization module comprises an electronic control member, the electronic control member is electrically connected to the hydroelectric power module and the UV source, the UV source has an electrical connection surface electrically connected to the electronic control member, a cooling channel is between the electrical connection surface of the UV source and the electronic control member, the cooling channel communicates with the inlet end and the outlet end.

3. The UV sterilization tube of claim 2, wherein the water flow flows through the cooling channel and the sterilization channel.

4. The UV sterilization tube of claim 3, wherein one end of the cooling channel is connected to the inlet end of the hollow tube, and another end thereof is connected to the sterilization channel; one end of the sterilization channel is connected to the outlet end of the hollow tube, and another end thereof is connected to the cooling channel.

5. The UV sterilization tube of claim 3, wherein one end of the sterilization channel is connected to the inlet end of the hollow tube, and another end thereof is connected to the cooling channel; one end of the cooling channel is connected to the outlet end of the hollow tube, and another end thereof is connected to the sterilization channel.

6. The UV sterilization tube of claim 2, wherein the cooling channel and the sterilization channel are connected to form a zigzag flow route.

7. The UV sterilization tube of claim 6, wherein the cooling channel and the sterilization channel are substantially parallel to each other, and the cooling channel is connected to the sterilization channel through a side channel.

8. The UV sterilization tube of claim 2, wherein the electrical connected surface and the light-emitting surface of the UV light source are positioned on different sides.

9. The UV sterilization tube of claim 2, wherein the electrical connected surface and the light-emitting surface of the UV light source are positioned back-to-back.

10. The UV sterilization tube of claim 2, wherein the electrical connected surface of the UV light source faces to the electronic control member.

11. The UV sterilization tube of claim 2, wherein the water flow does not flow between the hydroelectric power module and the electronic control member.

12. The UV sterilization tube of claim 2, wherein the electronic control member is positioned between the hydroelectric power module and the UV source.

13. The UV sterilization tube of claim 2, wherein the UV source is positioned between the electronic control member and the reflector.

14. The UV sterilization tube of claim 1, wherein the hydroelectric power module is positioned between the UV sterilization module and the inlet end.

15. The UV sterilization tube of claim 14, wherein the hydroelectric power module has a water-driven blade assembly facing to the inlet end, whereby the water flow may drive the water-driven blade assembly to rotate.

16. The UV sterilization tube of claim 1, wherein the hydroelectric power module is positioned between the UV sterilization module and the outlet end.

17. The UV sterilization tube of claim 16, wherein the hydroelectric power module has a water-driven blade assembly positioned back-to-back to the outlet end, whereby the water flow may drive the water-driven blade assembly to rotate.

18. The UV sterilization tube of claim 1, wherein the reflector has a reflection surface facing to the light-emitting surface of the UV source.

* * * * *